(12) United States Patent
Govrin et al.

(10) Patent No.: US 10,887,992 B2
(45) Date of Patent: *Jan. 5, 2021

(54) CAMERA HEAD

(71) Applicant: MEDIGUS Ltd., Omer (IL)

(72) Inventors: Amir Govrin, Ramat Gan (IL); Minelu Sonnenschein, Meitar (IL)

(73) Assignee: MEDIGUS LTD., Omer (IL)

(*) Notice: Subject to any disclaimer, the term of this patent is extended or adjusted under 35 U.S.C. 154(b) by 0 days.

This patent is subject to a terminal disclaimer.

(21) Appl. No.: 16/534,559

(22) Filed: Aug. 7, 2019

(65) Prior Publication Data
US 2019/0364661 A1 Nov. 28, 2019

Related U.S. Application Data

(63) Continuation of application No. 15/579,410, filed as application No. PCT/IL2016/050603 on Jun. 9, 2016, now Pat. No. 10,420,216.

(30) Foreign Application Priority Data

Jun. 11, 2015 (IL) .......................................... 239386

(51) Int. Cl.
H05K 1/00 (2006.01)
H05K 1/14 (2006.01)
(Continued)

(52) U.S. Cl.
CPC ............. *H05K 1/144* (2013.01); *A61B 1/051* (2013.01); *A61B 1/0607* (2013.01);
(Continued)

(58) Field of Classification Search
USPC ............................................................ 348/68
See application file for complete search history.

(56) References Cited

U.S. PATENT DOCUMENTS 4,491,865 A 1/1985 Danna et al.
5,309,324 A 5/1994 Herandez et al.
(Continued)

FOREIGN PATENT DOCUMENTS

DE 10 2006 019511 A1 10/2007
JP 2005-074034 A 3/2005
(Continued)

OTHER PUBLICATIONS

International Preliminary Report on Patentability for PCT/IL2016/050603, dated Nov. 8, 2017 (11 pages).
(Continued)

Primary Examiner — Behrooz M Senfi
(74) Attorney, Agent, or Firm — Roach, Brown, McCarthy & Gruber, P.C.; Kevin D. McCarthy

(57) ABSTRACT

A video camera head is comprised of at least two rigid printed circuit boards (PCBS) arranged in parallel planes. The at least two PCBs are mechanically supported one above the other by pins made of an electricity conducting material that conduct electrical power from the bottom PCB to electronic components or illumination means mounted on the other PCBs and signals from a solid state sensor chip mounted on one of the other PCBs of the at least two PCBs to the bottom PCB. Several embodiments of the video camera head are described.

17 Claims, 3 Drawing Sheets

(51) Int. Cl.
    *H04N 5/225*     (2006.01)
    *A61B 1/05*     (2006.01)
    *A61B 1/06*     (2006.01)
    *G02B 23/24*     (2006.01)

(52) U.S. Cl.
    CPC .......... *A61B 1/0676* (2013.01); *A61B 1/0684* (2013.01); *G02B 23/243* (2013.01); *G02B 23/2469* (2013.01); *G02B 23/2484* (2013.01); *H04N 5/2257* (2013.01); *H05K 2201/042* (2013.01); *H05K 2201/09027* (2013.01); *H05K 2201/10106* (2013.01); *H05K 2201/10121* (2013.01); *H05K 2201/10151* (2013.01); *H05K 2201/10303* (2013.01); *H05K 2201/10318* (2013.01); *H05K 2201/2036* (2013.01)

(56) References Cited

U.S. PATENT DOCUMENTS

| | | | |
|---|---|---|---|
| 6,817,870 | B1 | 11/2004 | Kwong et al. |
| 7,474,390 | B2 | 1/2009 | Robinson et al. |
| 10,420,216 | B2* | 9/2019 | Govrin ............... G02B 23/2469 |
| 10,426,324 | B2* | 10/2019 | Nakamura ............... A61B 1/04 |
| 2004/0171914 | A1* | 9/2004 | Avni ................... H05K 3/3436 |
| | | | 600/160 |
| 2010/0185052 | A1* | 7/2010 | Chang ................... A61B 1/051 |
| | | | 600/112 |
| 2012/0206583 | A1 | 8/2012 | Hoshi et al. |
| 2013/0050954 | A1 | 2/2013 | Albrecht, III et al. |
| 2013/0155396 | A1 | 6/2013 | Deliwala |
| 2013/0303003 | A1 | 11/2013 | Tsang et al. |
| 2014/0296628 | A1 | 10/2014 | Kirma et al. |
| 2015/0342690 | A1* | 12/2015 | Zubiate ................. A61B 1/051 |
| | | | 606/130 |
| 2017/0095142 | A1* | 4/2017 | McDowall ......... G02B 23/2415 |

FOREIGN PATENT DOCUMENTS

| | | |
|---|---|---|
| JP | 2012-205849 A | 10/2012 |
| WO | 2011/033513 A1 | 3/2011 |
| WO | 2011030608 A1 | 2/2013 |

OTHER PUBLICATIONS

Written Opinion of the International Searching Authority for PCT/IL2016/050603, dated Sep. 25, 2016 (5 pages).

International Search Report for PCT/IL2016/050603, dated Sep. 25, 2016 (3 pages).

Communication—Supplementary European Search Report—from a foreign patent office—European Patent Office—in a counterpart foreign application—EP 16 80 7031—dated Jan. 9, 2019; 9 pages.

Corresponding Japanese Patent Application No. 2017-563521 in an Office Action dated Jun. 16, 2020 (5 pages for Japanese language office action and 6 pages for a machine English translation).

* cited by examiner

CAMERA HEAD

FIELD OF THE INVENTION

The invention is from the field of video cameras. Specifically the invention relates to small diameter camera heads for use in such applications as medical endoscopes and laparoscopes and industrial borescopes.

BACKGROUND OF THE INVENTION

Ever since their first use it has been the goal of designers of medical endoscopes and laparoscopes and industrial borescopes to reduce the diameter of the instruments in order to allow access through smaller and smaller diameter orifices.

Methods of accomplishing reductions in the diameter are discussed for example in WO2011/033513 in which the Applicant of the present invention describes camera heads having an outer diameter of 1.4 mm or less.

Two of the obstacles to even further reduction in diameter are the flexible PCB substrates on which the sensor and other components of the camera head are generally mounted and the internal wiring that electrically connects the various electronic components. A third obstacle connected with small diameter camera heads such as those described in WO2011/033513 is the difficulty of assembly, in particular connecting the internal wiring, which is not suitable to mass production manufacturing.

A fourth obstacle is related to the need of integrated illumination in the aforementioned devices and the difficulty of transferring adequate amounts of current while maintaining the minimal dimensions of the camera-illumination assembly.

It is therefore a purpose of the present invention to provide a camera head which addresses the above mentioned obstacles.

Further purposes and advantages of this invention will appear as the description proceeds.

SUMMARY OF THE INVENTION

In a first aspect the invention is a video camera head comprised of at least two rigid printed circuit boards (PCBs) arranged in parallel planes. The PCBs are mechanically supported one above the other by pins made of an electricity conducting material. The pins conduct electrical power from the bottom PCB to electronic components and/or illumination means mounted on the other PCBs of the at least two PCBs and signals from a sensor chip mounted on one of the other PCBs of the at least two PCBs to the bottom PCB.

In embodiments of the video camera head of the invention the illumination means comprise at least one LED, e.g. a ring array of LEDs.

Embodiments of the video camera head of the invention comprise an objective optical system.

In embodiments of the video camera head of the invention comprised of three PCBs components for receiving signals from a solid state sensor and outputting a video signal are mounted on the bottom PCB, a solid state sensor chip is mounted on the middle PCB, and an objective optical system and illumination means are mounted on the top PCB. Pins made of electricity conducting material (a) mechanically support the middle and top PCBs above the bottom PCB, (b) conduct electrical power from the bottom PCB to the middle and top PCBs, and (c) conduct signals from the sensor chip on the middle PCB to the bottom PCB.

In embodiments of the video camera head of the invention comprised of two PCBs electronic components for receiving signals from a solid state sensor and outputting a video signal are mounted on the bottom PCB, a solid state sensor chip is mounted on the top side of the bottom PCB, and an objective optical system and illumination means are mounted on the top PCB. Pins made of electricity conducting material mechanically support the top PCB above the bottom PCB and conduct electrical power from the bottom PCB to top PCB. Through vias are provided to conduct electrical power from the bottom side to the top side of the bottom PCB and to conduct signals from the sensor chip on the top side to the bottom side of the bottom PCB.

In embodiments of the video camera head of the invention comprised of four PCBs, electronic components for receiving signals from a solid state sensor and outputting a video signal are mounted on the first (bottom) and second PCBs, a solid state sensor chip is mounted on the third PCB, and an objective optical system and illumination means are mounted on the fourth (top) PCB. Pins made of electricity conducting material (a) mechanically support the second, third, and fourth PCBs above the first PCB, (b) conduct electrical power from the first PCB to the second, third, and fourth PCBs, and (c) conduct signals from the sensor chip on the third PCB to the first PCB.

In a second aspect the invention is a video camera head comprised of at least two rigid printed circuit boards (PCBS) arranged in parallel planes. In the camera head of this aspect an objective optical system and illumination means are mounted on the distal end of a housing of the camera head, a solid state sensor chip is mounted on a PCB below the objective optical system, electronic components for receiving signals from a solid state sensor and outputting a video signal are mounted on at least one of the PCBs, the at least two PCBs are mechanically supported one above the other by electrically conducting pins, and the illumination means supported on the distal end of the camera housing are output couplers of optical fibers or the distal end of light guides.

The light source for the illumination means of the video camera of the second aspect of the invention can be any conventional light source used with endoscopic systems. In these embodiments the light from the LEDs is transferred to the distal end of a housing of the camera head through hollow light guides.

In embodiments of the video camera of the second aspect of the invention the light source is LEDs that are mounted on one of the PCBs in the camera head or proximally from it. The LEDs can be mounted on a PCB together with the solid state sensor chip.

In other embodiments the LEDs are mounted on a PCB below the PCB on which the solid state sensor chip is mounted.

In embodiments of the video camera of the second aspect of the invention the light source is located remotely from the camera head and the light is transferred directly from the light source to an output coupler on the distal end of the camera housing or to one of the PCBs where it is coupled into a hollow light guide.

In embodiments of the video camera head of the invention the pins can be either rigid or flexible.

In embodiments of the video camera head of the invention the PCBs are not circular and can have any shape, symmetric or non-symmetric.

In embodiments of the video camera head of the invention some or all of the PCBs in a camera head can be different from the shapes and dimensions of other PCBs in the camera head.

In embodiments of the video camera head of the invention some or all of the components of the objective optical system can be mounted on a housing of the camera head.

All the above and other characteristics and advantages of the invention will be further understood through the following illustrative and non-limitative description of embodiments thereof, with reference to the appended drawing.

DETAILED DESCRIPTION OF EMBODIMENTS OF THE INVENTION

Figure 1:
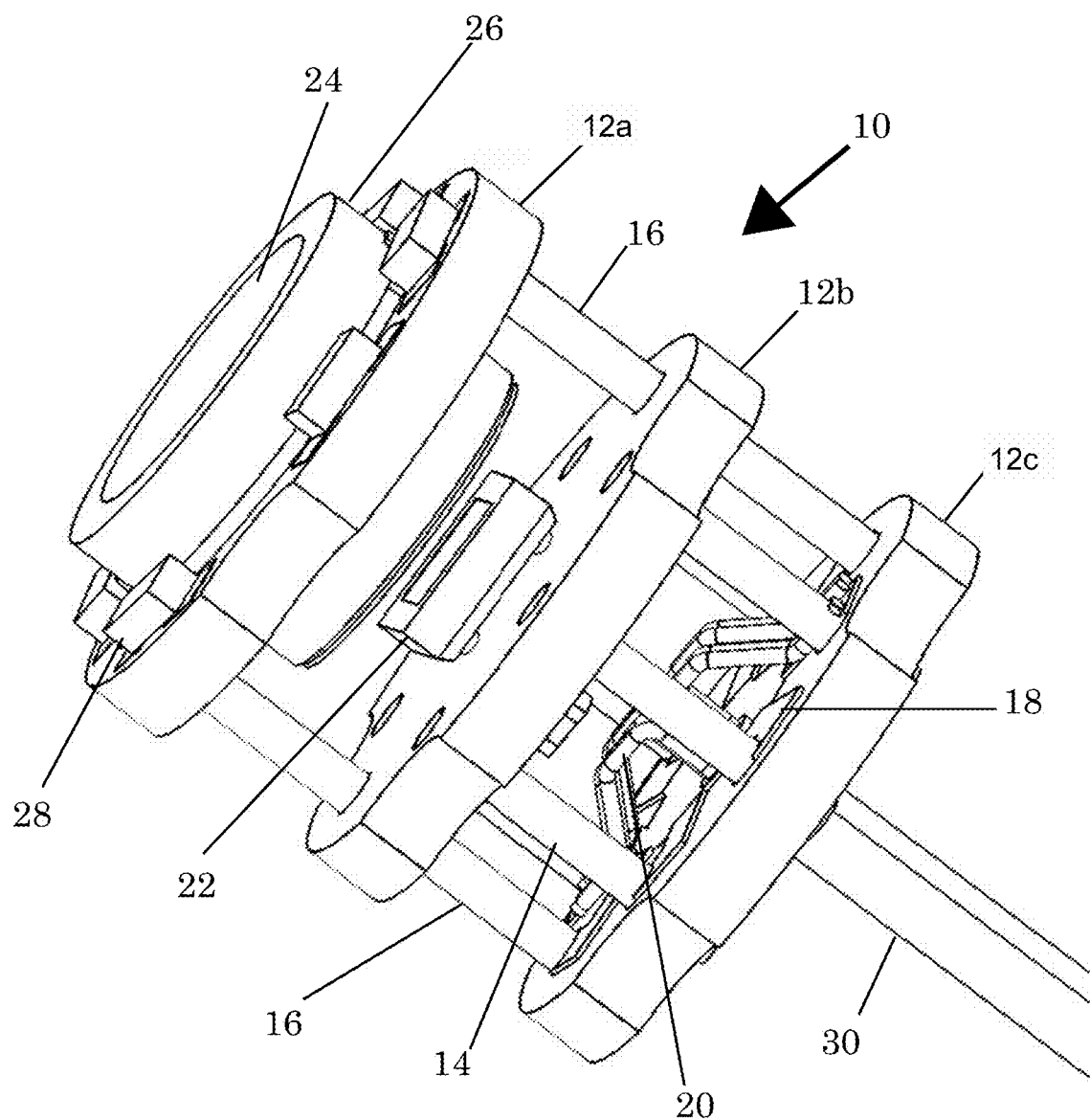
FIG. 1 schematically shows the structure of one embodiment of the camera head of the invention.

FIG. 1 schematically shows the structure of an embodiment of the camera head (10) of the invention. This embodiment of the camera head of the present invention comprises three rigid PCBs (12a, 12b, and 12c). The three PCBs are arranged in three parallel planes one above the other. (Note that for convenience the camera head is described as if it were oriented with its central axis vertical. This defines the relative directions such as top and bottom used herein.)

Figure 2:
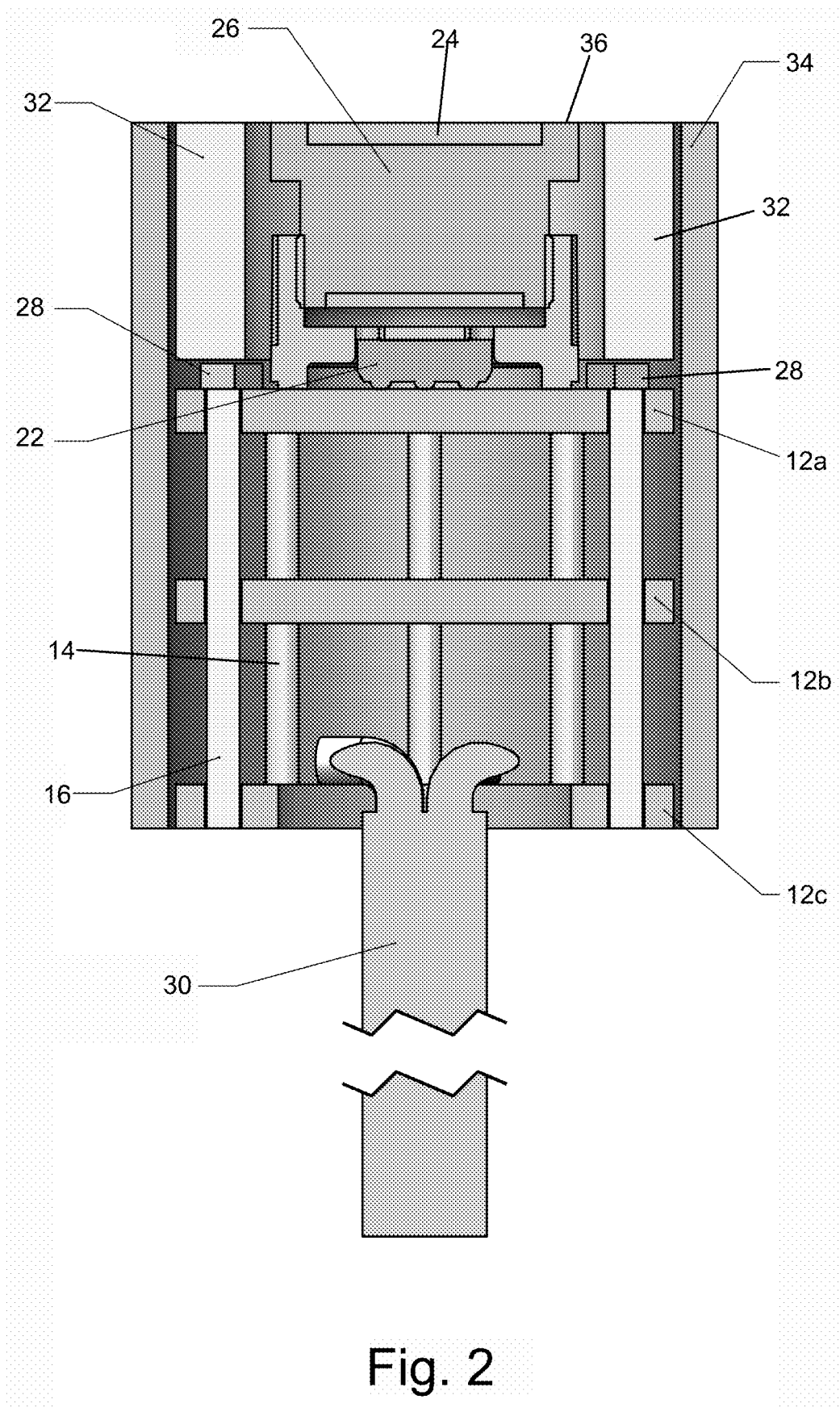
FIG. 2 and FIG. 3 schematically show a second embodiment of the camera head of the invention.
Figure 3:
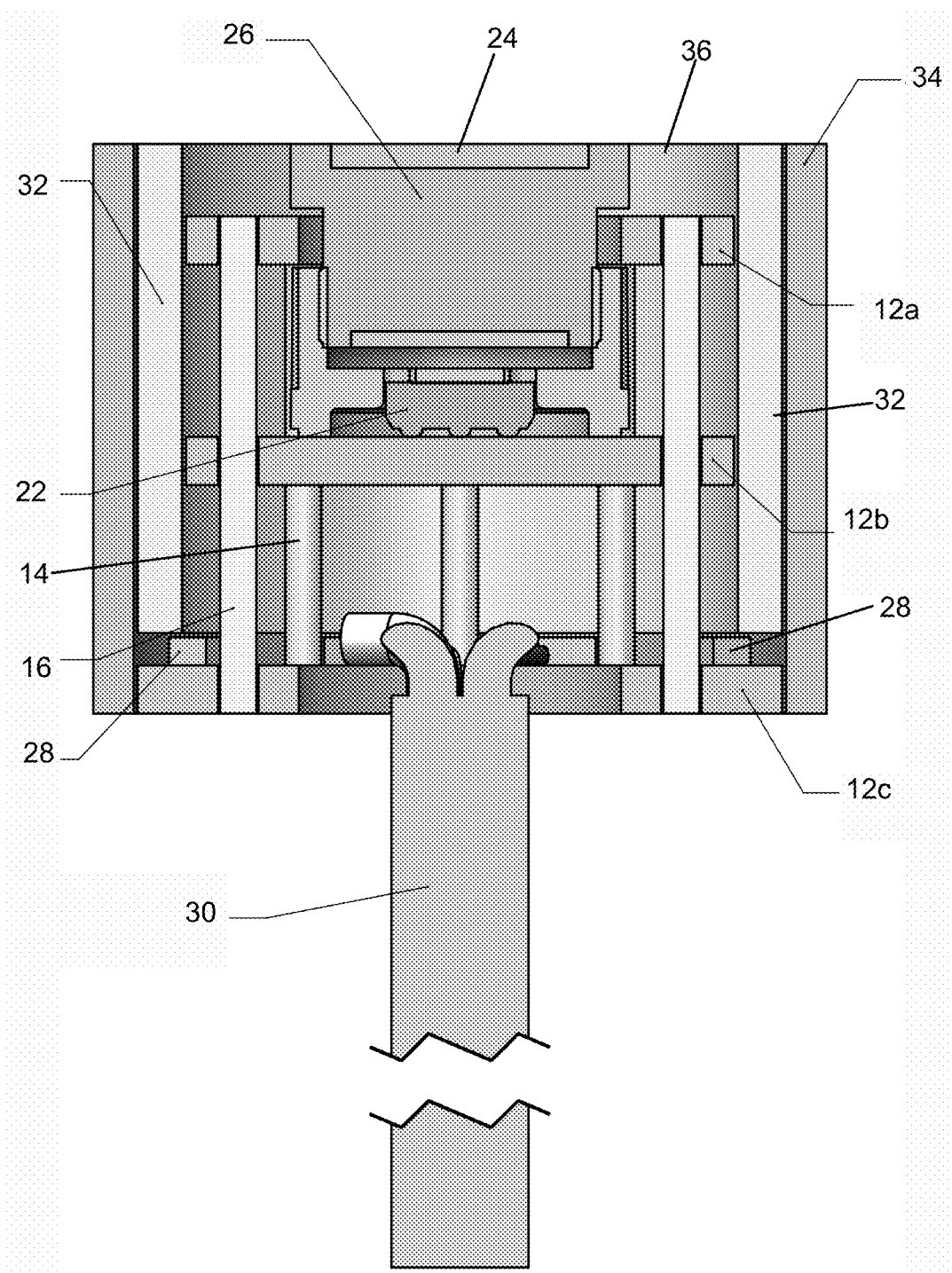

The middle PCB (12b) is mechanically supported above the lower PCB (12c) by six short pins (14) and the upper PCB (12a) is mechanically supported above the lower PCB (12c) by two longer pins (16) that pass through vias in PCB (12b). It is noted that embodiments of the camera head (10) may comprise more or less than 6 pins (14) and more than two pins (16). As is shown in FIGS. 1-3, all pins are located within the surface area of each of the PCBs and pass through vias in a PCB to reach the PCB above it.

Metallization (18) is created on the surface of the lower PCB (12c) and electronic components (20) for receiving signals from a solid state image sensor, e.g. CMOS, and outputting a video signal are electrically connected to this metallization. A camera cable (30) that conducts power to the camera head and video signals from it to a remote signal processor is connected by means of through vias to the metallization pattern on the top side of PCB (12c).

Middle PCB (12b) supports the solid state sensor chip (22).

The upper PCB (12a) supports the objective optical system (24) inside its housing (26) and illumination means, e.g. at least one LED or a ring array of LEDs (28) surrounding housing (26).

Pins (14) and (16) are made of electricity conducting material. Therefore they serve the dual purpose of mechanically supporting the upper two PCBs and also of conducting power to and signals from the sensor chip (22) and power to LEDs 28.

The internal structure of camera head (10) thus addresses all four of the obstacles discussed in the background section of this application. Firstly use of rigid PCBs instead of flexible PCBs eliminates the bending radius of the flexible PCB that usually increases the diameter of the camera head. Secondly the use of the electrically connecting pins allows for transferring adequate amounts of current for the illumination sources. Thirdly and fourthly the use of the electrically connecting pins eliminates most of the difficulty of making the internal wiring connections and therefore greatly simplifies the assembly process, thereby making camera head (10) into a device that is very suitable for mass production manufacturing.

It is noted that an embodiment of the camera head of the invention can comprise two PCBs in which case the electronic components are located on the bottom surface of the lower PCB and the sensor chip on the top surface of the bottom PCB and the objective lens system and illumination source on the upper PCB. Other embodiments can comprise more than three PCBs, for example four in which the lower two PCBs support electronic components, the third PCB supports the sensor chip and the top PCB supports the objective optical system and illumination means. In all embodiments electricity conducting pins serve the dual purposes of separating and mechanically supporting the PCBs and of conducting electric power and video signals between them.

In other embodiments of the invention the illumination means supported on the uppermost PCB are output couplers of optical fibers or light guides. In these embodiments the light source can be any conventional light source used with endoscopic systems, e.g. LEDs that can be mounted on one of the lower PCBs in the camera head or proximally from it. In some embodiments the electrically conducting pins may be combined with hollow light guides.

In one embodiment, shown schematically in FIG. 2, the camera head comprises three PCBs that are mechanically supported one above the other by electricity conducting pins 14,16. The two lower PCBs 12b,12c support electronic components (not shown in the figure) for receiving signals from a solid state image sensor 22 and outputting a video signal. The uppermost PCB 12a supports the solid state sensor 22 and one or more LEDs 28, e.g. a circular array, which surround the sensor. In this embodiment an objective lens system 24 enclosed in its housing 26 is held in place above the sensor 22 by a support structure, e.g. a hollow tube attached at its bottom end to the PCB 12a or by a structure attached to a camera housing 34 that surrounds the internal components of the camera head. The camera head also comprises vertical tubular light guides 32, which transfer light from the LEDs 28 to the height of the objective lens 24 on the distal end 36 of the camera housing 34 facing the object to be imaged. The light guides 32 are supported above the LEDs 28, for example by being attached at their bottom ends to the PCB 12a or by supports attached to the interior of the camera housing 34.

The electronic components located on PCBs 12a and 12b can be redistributed onto one PCB only and/or some can be located on PCB 12a thereby allowing this embodiment of the camera head to comprise only two PCBs. In all embodiments camera cable 30 is connected to electronic components on the bottom PCB.

A variation of the embodiment shown in FIG. 2 is shown schematically in FIG. 3. In the camera head shown in FIG. 3, electronic components (not shown) are located on PCBs 12a and 12c (and in some versions also on 12b), the LEDs 28 are on PCB 12c and light guides 32 transfer light from the LEDs 28 to the height of the objective lens 24 the distal end 36 of the camera housing 34 facing the object to be imaged.

In other embodiments the light source can be located remotely from the camera head and the light transferred directly from the light source to an output coupler on the distal end 36 of the camera housing 34 or alternately to one of the PCBs where it is coupled into a hollow light guide as shown in FIGS. 2 and 3.

Although embodiments of the invention have been described by way of illustration, it will be understood that the invention may be carried out with many variations, modifications, and adaptations, without exceeding the scope of the claims, for example:

a) the pins may be rigid or flexible;
b) the shape of the PCBs is not circular but can be any shape symmetric, e.g. square or rectangular, or asymmetric;
c) the shapes and dimensions of some or all of the PCBs in a camera head can be different from the shapes and dimensions of other PCBs in the camera head; and
d) in embodiments of the camera head, some or all of the components of an objective optical system can be mounted on the housing of the camera head.

The invention claimed is:

1. A video camera head comprised of at least two rigid printed circuit boards (PCBS) arranged in parallel planes; wherein,
   i) all of the at least two PCBs are mechanically supported one above the other by rigid pins;
   ii) the rigid pins are made of an electricity conducting material;
   iii) at least some of the rigid pins conduct electrical power from a bottom PCB to electronic components or illumination means mounted on other PCBs of the at least two PCBs;
   iv) some of the rigid pins conduct signals from a solid state sensor chip mounted on one of the other PCBs of the at least two PCBs to the bottom PCB;
   v) all of the rigid pins are located within the surface area of each of the PCBs and pass through vias created in the PCBs; and
   vi) at least some of the rigid pins are long rigid pins that support an uppermost PCB of the at least two PCBs above the bottom PCB and pass through vias created in any intermediate PCBs.

2. The video camera head of claim 1 wherein the illumination means comprise at least one LED.

3. The video camera head of claim 2 wherein the illumination means comprise a ring array of LEDs.

4. The video camera head of claim 1 comprising an objective optical system.

5. The video camera head of claim 1 comprised of three PCBs, wherein electronic components for receiving signals from a solid state sensor and outputting a video signal are mounted on the bottom PCB, a solid state sensor chip is mounted on the middle PCB, an objective optical system and illumination means are mounted on the top PCB, and pins made of electricity conducting material (a) mechanically support the middle and top PCBs above the bottom PCB,(b) conduct electrical power from the bottom PCB to the middle and top PCBs, and (c) conduct signals from the sensor chip on the middle PCB to the bottom PCB.

6. The video camera head of claim 1 comprised of two PCBs, wherein electronic components for receiving signals from a solid state sensor and outputting a video signal are mounted on the bottom PCB, a solid state sensor chip is mounted on the top side of the bottom PCB, an objective optical system and illumination means are mounted on the top PCB, and pins made of electricity conducting material mechanically support the top PCB above the bottom PCB and conduct electrical power from the bottom PCB to top PCB, and through vias are used to conduct electrical power from the bottom side to the top side of the bottom PCB and to conduct signals from the sensor chip on the top side to the bottom side of the bottom PCB.

7. The video camera head of claim 1 comprised of four PCBs, wherein electronic components for receiving signals from a solid state sensor and outputting a video signal are mounted on the first (bottom) and second PCBs, a solid state sensor chip is mounted on the third PCB, an objective optical system and illumination means are mounted on the fourth (top) PCB, and pins made of electricity conducting material (a) mechanically support the second, third, and fourth PCBs above the first PCB, (b) conduct electrical power from the first PCB to the second, third, and fourth PCBs, and (c) conduct signals from the sensor chip on the third PCB to the first PCB.

8. A video camera head comprised of at least two rigid printed circuit boards (PCBS) arranged in parallel planes, wherein an objective optical system and illumination means are mounted on the distal end of a housing of the camera head, a solid state sensor chip is mounted on a PCB below the objective optical system, electronic components for receiving signals from a solid state sensor and outputting a video signal are mounted on at least one of the PCBs, the at least two PCBs are mechanically supported one above the other by electrically conducting rigid pins, and the illumination means supported on the distal end of the camera housing are output couplers of optical fibers or the distal end of light guides; wherein:
   i) at least some of the rigid pins conduct electrical power from a bottom PCB to electronic components or illumination means mounted on other PCBs of the at least two PCBs;
   ii) some of the rigid pins conduct signals from a solid state sensor chip mounted on one of the other PCBs of the at least two PCBs to the bottom PCB;
   iii) all of the rigid pins are located within the surface area of each of the PCBs and pass through vias created in the PCBs; and
   iv) at least some of the rigid pins are long rigid pins that support an uppermost PCB of the at least two PCBs above the bottom PCB and pass through vias created in any intermediate PCBs.

9. The video camera of claim 8 wherein a light source for the illumination means is any conventional light source used with endoscopic systems.

10. The video camera of claim 9 wherein the light source is at least one LED that is mounted on one of the PCBs in the camera head or proximally from it.

11. The video camera of claim 10 wherein the light from the at least one LED is transferred to the distal end of a housing of the camera head through hollow light guides.

12. The video camera of claim 10 wherein the at least one LED is mounted on a PCB together with the solid state sensor chip.

13. The video camera of claim 10 wherein the at least one LED is mounted on a PCB below the PCB on which the solid state sensor chip is mounted.

14. The video camera of claim 9 wherein the light source is located remotely from the camera head and the light is transferred directly from the light source to an output coupler on the distal end of the camera housing or to one of the PCBs where it is coupled into a hollow light guide.

15. The video camera of claim 1 wherein the PCBs are of any shape, symmetric or non-symmetric.

16. The video camera of claim 1 wherein the shapes and dimensions of some or all of the PCBs in a camera head are different from the shapes and dimensions of other PCBs in the camera head.

17. The video camera of claim 8 wherein some or all of the components of the objective optical system are mounted on the housing of the camera head.

* * * * *